(12) United States Patent
Ehmann et al.

(10) Patent No.: US 7,186,554 B2
(45) Date of Patent: Mar. 6, 2007

(54) METHODS AND COMPOSITIONS FOR HUMAN BLADDER EPITHELIAL CELL CULTURE

(75) Inventors: Ursula K. Ehmann, Woodside, CA (US); Martha K. Terris, Martinez, GA (US)

(73) Assignee: Stanford University, Palo Alto, CA (US)

( * ) Notice: Subject to any disclaimer, the term of this patent is extended or adjusted under 35 U.S.C. 154(b) by 0 days.

(21) Appl. No.: 10/767,630

(22) Filed: Jan. 28, 2004

(65) Prior Publication Data

US 2005/0014253 A1    Jan. 20, 2005

Related U.S. Application Data

(60) Provisional application No. 60/443,027, filed on Jan. 28, 2003.

(51) Int. Cl.
C12N 5/00 (2006.01)
C12N 5/08 (2006.01)
(52) U.S. Cl. ................ 435/373; 435/371; 435/378; 435/395; 435/325
(58) Field of Classification Search ................ 435/347, 435/371, 373, 4
See application file for complete search history.

(56) References Cited

U.S. PATENT DOCUMENTS 5,643,787 A * 7/1997 Barsky et al. .............. 435/371

FOREIGN PATENT DOCUMENTS

WO    WO 9307913 A1 * 4/1993

OTHER PUBLICATIONS

Logothetou-Rella et al. Growth characteristics of cultured human normal bladder epithelial cells: a comparison with urothelial carcinoma cell cultures. Eur Urol. vol. 15, No. 3-4, pp. 259-263, 1988.*
Crook et al. A model of superficial bladder cancer using fluorescent tumour cells in an organ-culture system. BJU Int. vol. 86, No. 7, pp. 886-893, Nov. 2000.*
Anderson.Molecular structure of tight junctions and their role in epithelial transport. News Physiol Sci. vol. 16, pp. 126-130, Jun. 2001.*
Taylor-Papadimitriou et al. Growth requirements of human mammary epithelial cells in culture, Int J Cancer. 15;20(6):903-8, Dec. 1977.*
Smith et al. Clonal proliferation of cultured nonmalignant and malignant human breast epithelia.□□Cancer Res. 41(11 Pt 1):4637-43, Nov. 1981.*
Fentiman et al. Cultured human breast cancer cells lose selectivity in direct intercellular communication. Nature. 269(5624):156-8, Sep. 1977.*
Southgate et al. "Culture of Human Urothelium" in Culture of Epithlial Cells, Second Edition. Edited by R. Ian Freshney and Mary G. Freshney, Wiley-Liss, Inc., 2002, pp. 381-399.*

Ehmann et al. Physical connections between feeder cells and recipient normal mammary epithelial cells. Exp Cell Res. 243(1):76-86, Aug. 1998.*
Vatne et al. A human in vitro model of bladder rumour cell invasion. Anticancer Res. 18(6A):3985-9, Nov.-Dec. 1998.*
Atala, A. et al. 1992 "Formation of urothelial structures in vivo from dissociated cells attached to biodegradable polymer scaffolds in vitro." *J Urol*, 148: 658-662.
Atala, A. et al. 1993 "Implantation in vivo and retrieval of artificial structures consisting of rabbit and human urothelium and human bladder muscle." *J Urol*, 150: 608-612.
Birchmeier, W. et al. 1994 "Cadherin expression in carcinomas: role in the formation of cell junctions and the prevention of invasiveness." *Biochim Biophys Acta*, 1198:11-26.
Bulbul, M.A. et al. 1986 "Growth of human urologic tumors on extracellular matrix." *J Urol*, 136: 512-516.
Chlapowski, F.J. 1989 "Long term growth and maintenance of stratified rat urothelium in vitro." *Cell Tissue Kinet*, 22: 245-257.
Cilento, B.G. et al. 1994 "Phenotypic and cytogenetic characterization of human bladder urothelia expanded in vitro." *J Urol*, 152: 665-670.
De Boer, W. I. et al. 1994 "Characterization of distinct functions for growth factors in murine transitional epithelial cells in primary organotypic culture." *Exp Cell Res*, 214:510-518.
Dulbecco, R. et al. 1979 "Differentiation of a rat mammary cell line in vitro." *PNAS USA*, 76:1256-1260.
Ehmann U.K. et al. 2002 "Juxtacrine stimulation of normal and malignant human bladder epothelial cell proliferation." *J. Urol*, 167:735-741.
Ehmann, U.K. et al. 1984 "To grow mouse mammary epithelial cells in culture." *J Cell Biol*, 98: 1026-1032.
Freeman, M.R. et al. 1997 "Heparin-binding EGF-like growth factor is an autocrine growth factor for human urothelial cells and is synthesized by epithelial smooth muscle cells in the human bladder." *J Clinical Invest*, 99:1028-1036.
Fujiyama, C. et al. 1995 "Reconstruction of the urinary bladder mucosa in three-dimensional collagen gel culture: fibroblast-extracellular matrix interactions on the differentiation of transitional epithelial cells." *J Urol*, 153: 2060-2067.
Guhe, C. et al. 1994 "Growth and characterization of porcine urinary bladder epithelial cells in vitro." *Am J Physiol*, 266: F298-F308.
Hammond, S.L. et al. 1984 "Serum-free growth of human mammary epithelial cells: Rapid clonal growth in defined medium and extended serial passage with pituitary extract." *PNAS USA*, 81:5435-5439.
Hicks, R.H. 1975 "The mammalian bladder: an accommodating organ." *Biol Rev*, 50: 215-246.
Hutton, K.A. et al. 1993 "Urothelial tissue culture for bladder reconstruction: an experimental study." *J Urol*, 150: 721-725.
Johnson, M.D. et al. 1985 "Serial cultivation of normal rat bladder epithelial cells in vitro." *J Urol*, 133: 1076-1081.

(Continued)

Primary Examiner—Celine Qian
Assistant Examiner—Jennifer Dunston
(74) Attorney, Agent, or Firm—Knobbe, Martens, Olson & Bear, LLP (57) ABSTRACT

The present invention provides methods for culturing normal and malignant human bladder epithelial cells for many generations, and compositions of matter to be used in the methods.

2 Claims, 7 Drawing Sheets

OTHER PUBLICATIONS

Kirk, D. et al. 1985 "Selective growth of normal adult human urothelial cells in serum-free medium." *In Vitro Cell Dev Biol*, 21: 165-171.

Masters, J.R. et al. 1986 "Tissue culture model of transitional cell carcinoma: characterization of twenty-one human urothelial cell lines." *Cancer Res*, 46:3630-3636.

Nguyen, H.T. et al. 1999 "Cell-Specific activation of the HB-EGF and ErbB1 genes by stretch in primary human bladder cells." *In Vitro Cell Dev Biol Animal*, 35:371-375.

Otto, T. et al. 1994 "Inverse relation of E-cadherin and autocrine motility factor receptor expression as a prognostic factor in patients with bladder carcinomas." *Cancer Res*, 54: 3120-3123.

Petzoldt, J.L. et al. 1994 "Culture and characterisation of human urothelium in vivo and in vitro." *Urol Res*, 22: 67-74.

Reznikoff, C.A. et al. 1983 "Growth and characterization of normal human urothelium in vitro." *In Vitro*, 19: 326-343.

Shi, W. et al. 2000 "The tetraspanin CD9 associates with transmembrane TGF- and regulates TGF—induced EGF receptor activation and cell proliferation." *J Cell Biol*, 148:591-601.

Staack, A. et al. 2001 "Organ and species specificity in the stimulation of transitional epithelial cell growth by fibroblasts." *Eur Urol*, 39: 471-477.

Sterle, M. 1996 "Growth and differentiation of urothelial cells in explant culture." *Pflugers Arch*, 431: R245-R246.

Truschel, S.T. et al. 1999 "Primary uroepithelial cultures. A model system to analyze umbrella cell barrier function." *J Biol Chem*, 274:15020-15029.

Tzeng, C.-C. et al. 1996 "Characterization of two urothelium cancer cell lines derived from a blackfoot disease endemic area in Taiwan." *Anticancer Res*, 16:1797-1804.

Vatne, V. et al. 1998 "Nonadhesive stationary organ culture of normal human urinary bladder mucosa." *Anticancer Res*, 18:3979-3984.

Yu, H.J. et al. 1992 "Characteristics of a newly established human bladder carcinoma cell-line, NTUB1." *J Formosan Med Assoc*, 91:608-613.

* cited by examiner

METHODS AND COMPOSITIONS FOR HUMAN BLADDER EPITHELIAL CELL CULTURE

RELATED APPLICATIONS

This application claims the benefit of U.S. Provisional Application No. 60/443,027, filed Jan. 28, 2003.

FIELD OF THE INVENTION

The present invention provides methods for culturing normal and malignant human bladder epithelial cells for many generations, and compositions of matter to be used in the methods.

BACKGROUND OF THE INVENTION

Cultures of urothelial cells provide material for physiological studies and provide tissue matrices or matrix components for the surgical reconstruction of the genitourinary tract. Methods for culturing several types of animal and human urothelial cells have been reported. Several investigators have successfully cultured human bladder epithelial cells in serum-free media with low calcium concentrations and defined growth factors (see, e.g., Kirk, D. et al. 1985 In vitro *Cell Develop Biol* 21:165; Hutton, K. A. R. et al. 1993 *J Urol* 150:721; Petzoldt, J. L. et al. 1994 *Urol Res* 22:67; and Cilento, B. G. et al. 1994 *J Urol* 152:665). One group of investigators plated fibroblast feeder cells with human bladder epithelial cells. Another reported that medium conditioned by fibroblasts from the bladder was able to stimulate human bladder epithelial cell proliferation. Bladder epithelial cells have been cultured on various substrates, including collagen, extracellular matrix, and agar (see, e.g., Bulbul, M. A. et al. 1986 *J Urol* 136:512; Vatne, V. et al. 1998 *Anticancer Res* 18:3979). Atala, A. et al. 1993 *J Urol* 150:608 have achieved cell proliferation on synthetic polymers which could be implanted into animals without untoward effects.

Normal bladder includes a multilayered epithelium in which the basal layer rests on a basal lamina and the intermediate layers of cuboidal cells are covered by a superficial layer of "umbrella" cells. Umbrella cells contain fusiform vesicles, and have membranes that are asymmetrical and are comprised of uroplakin proteins (Hicks, R. H. 1975 *Biol Rev* 50:214). Umbrella cells line the luminal surface of the bladder, and the tight junctions joining them provide an effective barrier to the flux of particular ions. In addition, normal bladder cells express a number of specific keratins.

There is interest in the art to provide a robust in vitro multi-layered human epithelial bladder system that maintains the properties of in vivo human epithelial bladder cells, including expression of appropriate keratins. The present invention satisfies this interest.

SUMMARY OF THE INVENTION

The present invention provides methods and compositions of matter for culturing normal and malignant human bladder epithelial cells for many generations.

Thus, the present invention provides in one embodiment, a method of culturing human bladder epithelial cells or human epithelial cells of another luminal organ comprising plating a confluent monolayer of non-proliferating epithelial cells and human bladder epithelial cells or human epithelial cells of another luminal organ in medium on a culture support; and incubating the plated cells under conditions appropriate to allow the human bladder epithelial cells or human epithelial cells of another luminal organ to proliferate. In one aspect of this embodiment of the invention, the non-proliferating cells are cells with which the human epithelial cells form tight junctions. In another aspect of this embodiment of the invention, the non-proliferating cells are rat LA7 cells or other mammary cells.

In yet another embodiment of the present invention, there is provided a composition of matter consisting essentially of non-proliferating epithelial cells, human bladder epithelial cells or human epithelial cells of another luminal organ and medium. In one aspect of this embodiment of the invention, the non-proliferating cells are cells with which the human epithelial cells form tight junctions. In another aspect of this embodiment of the invention, the non-proliferating cells are rat LA7 cells or other mammary cells.

In another embodiment of the present invention, the methods and compositions of matter disclosed may be used to study the physiology of human bladder epithelium in various assays, including ion transport across cell membranes. In yet another embodiment of the present invention, the methods and compositions of matter disclosed may be employed on implant matrices or compounds of such matrices for use in human patients.

These and other objects, advantages, and features of the invention will become apparent to those persons skilled in the art upon reading the details of the compositions and methods more fully described below.

BRIEF DESCRIPTION OF THE DRAWINGS

So that the manner in which the above-recited features of the present invention can be understood in detail, a more particular description of the invention may be had by reference to the embodiments that are illustrated in the appended drawings. It is to be noted, however, that the appended drawings illustrate only typical embodiments of this invention and are therefore not to be considered limiting of its scope, for the invention may admit to other equally effective embodiments.

FIG. 4*a*–*f* shows normal human bladder epithelial cells in passage 6 with antibodies to keratins 18, 19, and 14. Bladder cells express keratins 18 and 19, as do normal bladder cells in vivo, but do not express keratin 14, which bladder cells in vivo also do not express.

FIG. 5*a*–*d* shows that normal human bladder epithelial cells in passage 6, incubated with an antibody to keratin 7, express keratin 7, as do normal cells in vivo.

FIG. 6*a*–*e* shows normal human bladder epithelial cells in passage 6 incubated with an antiserum to the tight junction ZO1 protein. Bladder cells connect to their neighboring bladder or LA7 feeder cells by tight junctions.

DETAILED DESCRIPTION OF THE PREFERRED EMBODIMENT

The present invention provides methods and devices that facilitate tissue reconstruction. In its broadest form, the methods and devices of the present invention are useful in the reconstruction, repair, augmentation or replacement of organs or tissues structures that comprise multilayer cellular organization and particularly those organs or tissue structures that are luminal in nature. More particularly, the present invention provides methods and devices that facilitate the reconstruction, repair, augmentation or replacement of shaped hollow organs or tissue structures that exhibit a laminar segregation of different cell types and that have a need to retain a general luminal shape. Luminal organs or tissue structures that contain a smooth muscle cell (SMC) layer to impart compliant or contractible properties to the organ or structure are particularly well suited to the methods and devices of the present invention.

In an example of one preferred embodiment of the invention, the luminal organ is the bladder, which has an inner layer of a first cell population that comprises urothelial cells and an outer layer of a second cell population that comprises smooth muscle cells. This organization is also present in other genitourinary organs and tissue structures such as the ureters and urethra. Laminarily organized organs or tissues refer to any organ or tissue made up of, or arranged in laminae including ductal tissue. Other suitable laminarily organized luminal organs, tissue structure, or ductal tissues to which the present invention is directed include vas deferens, fallopian tubes, lacrimal ducts, trachea, stomach, intestines, vasculature, biliary duct, ductus ejaculatorius, ductus epididymidis, and ductus parotideus.

The method of the present invention in its broadest aspect encompasses as a first step providing a biocompatible synthetic or natural polymeric matrix that is shaped to conform to its use as a part or all of the luminal organ or tissue structure to be repaired, reconstructed, augmented or replaced. A biocompatible material is any substance not having toxic or injurious effects on biological function. The shaped matrix is preferably porous to allow for cell deposition both on and in the pores of the matrix. The shaped polymeric matrix is then contacted, preferably sequentially, with at least one cell population supplied to the matrix to seed the cell population on and/or into the matrix. The seeded matrix is then implanted in the body of the recipient where the separate, laminarily organized cell populations facilitate the formation of neo-organs or tissue structures.

In a preferred embodiment, the materials and methods of the invention are useful for the reconstruction or augmentation of bladder tissue. Thus, the invention provides treatments for such conditions as bladder exstrophy, bladder volume insufficiency, reconstruction of bladder following partial or total cystectomy, repair of bladders damaged by trauma, and the like.

While reference is made herein to augmentation of bladder according to the invention, it will be understood that the methods and materials of the invention are useful for tissue reconstruction or augmentation of a variety of tissues and organs in a subject. Thus, for example, organs or tissues such as bladder, ureter, urethra, renal pelvis, and the like, can be augmented or repaired with polymeric matrixes seeded with cells. The materials and methods of the invention further can be applied to the reconstruction or augmentation of vascular tissue (see, e.g., Zdrahala, R. J. 1996 *J Biomater Appl* 10:309–29), intestinal tissues, stomach (see, e.g., Laurencin, C. T. et al. 1996 *J Biomed Mater Res* 30:133–8), and the like. The patient to be treated may be of any species of mammals such as a dog, cat, pig, horse, cow, or human, in need of reconstruction, repair, or augmentation of a tissue.

Biocompatible material and especially biodegradable material is the preferred material for the construction of the polymeric matrix. The polymeric matrix is used in the construction of the reconstructive urothelial graft (RUG). The RUG is an implantable, biocompatible, synthetic or natural polymeric matrix. The RUG is shaped to conform to at least a part of the luminal organ or tissue structure in need of treatment and has at least one cell population deposited either on or in the polymeric matrix. Thus the RUG is matrix/cell construct.

Biocompatible refers to materials which do not have toxic or injurious effects on biological functions. Biodegradable refers to material that can be absorbed or degraded in a patient's body. Examples of biodegradable materials include, for example, absorbable sutures. Representative materials for forming the biodegradable structure include natural or synthetic polymers, such as, for example, collagen, poly(alpha esters) such as poly(lactate acid), poly(glycolic acid), polyorthoesters and polyanhydrides and their copolymers, which degraded by hydrolysis at a controlled rate and are reabsorbed. These materials provide the maximum control of degradability, manageability, size and configuration. Preferred biodegradable polymer material include polyglycolic acid and polyglactin, developed as absorbable synthetic suture material. Polyglycolic acid and polyglactin fibers may be used as supplied by the manufacturer. Other biodegradable materials include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the RUG. Next a solvent is used to dissolve away one of the components, resulting in pore formation. (See, Mikos, U.S. Pat. No. 5,514,378). In nucleation, thin films in the shape of a RUG are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a RUG structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix may be weaved, compression molded and glued together. Furthermore different polymeric materials shaped by different processes may be joined together to form a composite shape. The composite shape may be a laminar structure. For example, a polymeric matrix may be attached to one or more polymeric matrixes to form a multilayer polymeric matrix structure. The attachment may be performed by gluing with a liquid polymer or by suturing. In addition, the polymeric matrix may be formed as a solid block and shaped by laser or other standard machining techniques to its desired final form. Laser shaping refers to the process of removing materials using a laser.

The biodegradable polymers can be characterized with respect to mechanical properties, such as tensile strength using an Instron tester, for polymer molecular weight by gel permeation chromatography (GPC), glass, transition temperature by differential scanning calorimetry (DSC) and bond structure by infrared (1R) spectroscopy; with respect to toxicology by initial screening tests involving Ames assays and in vitro teratogenicity assays and implantation studies in animals for immunogenicity, inflammation, release and degradation studies. In vitro cell attachment and viability can be assessed using scanning electron microscopy, histology and quantitative assessment with radioisotopes. The biodegradable material may also be characterized with respect to the amount of time necessary for the material to degrade when implanted in a patient. By varying the construction, such as, for example, the thickness and mesh size, the biodegradable material may substantially biodegrade between about 2 years or about 2 months, preferably between about 18 months and about 4 months, most preferably between about 15 months and about 8 months and most preferably between about 12 months and about 10 months. If necessary, the biodegradable material may be constructed so as not to degrade substantially within about 3 years, or about 4 years or about five or more years.

At the submicron level the polymeric matrix may be impermeable to bacteria, viruses and other microbes.

A mesh-like structure formed of fibers, which may be round, scalloped, flattened, star shaped, solitary or entwined with other fibers is advantageous. The use of branching fibers is based upon the same principles which nature has used to solve the problem of increasing surface area proportionate to volume increases. All multicellular organisms utilize this repeating branching structure. Branching systems represent communication networks between organs, as well as the functional units of individual organs. Seeding and implanting this configuration with cells allows implantation of large numbers of cells, each of which is exposed to the environment of the host, providing for free exchange of nutrients and waste while neovascularization is achieved. The polymeric matrix may be made flexible or rigid, depending on the desired final form, structure and function.

Polymeric matrixes can be treated with additives or drugs prior to implantation (before or after the polymeric matrix is seeded with cells), e.g., to promote the formation of new tissue after implantation. Thus, for example, growth factors, cytokines, extracellular matrix components, and other bioactive materials can be added to the polymeric matrix to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. *Vet. Surg.* 24 (5): 408–19 (1995)). For example, when polymeric matrixes (seeded with endothelial cells) are used to augment vascular tissue, vascular endothelial growth factor (VEGF) (see, e.g., U.S. Pat. No. 5,654,273) can be employed to promote the formation of new vascular tissue. Growth factors and other additives (e.g., epidermal growth factor (EGF), heparin-binding epidermal growth factor (HB-EGF), fibroblast growth factor (FGF), cytokines, genes, proteins, and the like) can be added in amounts in excess of any amount of such growth factors (if any) which may be produced by the cells seeded on the polymeric matrix. Such additives are preferably provided in an amount sufficient to promote the formation of new tissue of a type appropriate to the tissue or organ, which is to be repaired or augmented (e.g., by causing or accelerating infiltration of host cells into the graft). Other useful additives include antibacterial agents such as antibiotics.

One preferred supporting matrix is composed of crossing filaments which can allow cell survival by diffusion of nutrients across short distances once the cell support matrix is implanted. The cell support matrix becomes vascularized in concert with expansion of the cell mass following implantation.

The building of three-dimensional structure constructs in vitro, prior to implantation, facilitates the eventual terminal differentiation of the cells after implantation in vivo, and minimizes the risk of an inflammatory response towards the matrix, thus avoiding graft contracture and shrinkage.

The polymeric matrix may be shaped into any number of desirable configurations to satisfy any number of overall system, geometry or space restrictions. For example, in the use of the polymeric matrix for bladder reconstruction, the matrix may be shaped to conform to the dimensions and shapes of the whole or a part of a bladder. Naturally, the polymeric matrix may be shaped in different sizes and shapes to conform to the bladders of differently sized patients. Optionally, the polymeric matrix should be shaped such that after its biodegradation, the resulting reconstructed bladder may be collapsible when empty in a fashion similar to a natural bladder. The polymeric matrix may also be shaped in other fashions to accommodate the special needs of the patient. For example, a previously injured or disabled patient, may have a different abdominal cavity and may require a bladder reconstructed to adapt to fit. In other embodiments of the invention, the polymeric matrix is used for the treatment of laminar structures in the body such as urethra, vas deferens, fallopian tubes, lacrimal ducts. In those applications the polymeric matrix may be shaped as a hollow tube.

The polymeric matrix may be sterilized using any known method before use. The methods used depend on the material used in the polymeric matrix. Examples of sterilization methods include steam, dry heat, radiation, gases such as ethylene oxide, gas and boiling.

The RUG is constructed using urothelial cells from a donor. In an autologous RUG, the cells may be derived from the patient's own tissue such as, for example, from the bladder, urethra, ureter, and other urogenital tissue. In an allogeneic RUG, the cells may be derived from other member of the patient's species. In a xenogenic RUG, the cells may be derived from a species different from the patient. Donor cells may be from any urothelial cells origin and from any mammalian source such as, for example, humans, bovine, porcine, equine, caprine and ovine sources. Urothelial cells may be isolated in biopsies, or autopsies. In addition, the cells may be frozen or expanded before use.

Cells (such as autologous cells) must be cultured in vitro to increase the number of cells available for seeding on the polymeric matrix "scaffold". The use of allogenic cells, and more preferably autologous cells, is preferred to prevent tissue rejection. However, if an immunological response does occur in the subject after implantation of the RUG, the subject may be treated with immunosuppressive agents such as, for example, cyclosporin or FKSO6, to reduce the likelihood of rejection of the RUG. In certain embodiments, chimeric cells, or cells from a transgenic animal, can be seeded onto the polymeric matrix.

Cells may be transfected prior to seeding with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery. Urothelial cells could be transfected with specific genes prior to polymer seeding. The cell-polymer construct could carry genetic information required for the long term survival of the host or the tissue engineered neo-organ. For example, cells may be transfected to express insulin for the treatment of diabetes.

Seeding of cells onto the polymeric matrix can be performed, according to standard methods. For example, the seeding of cells onto polymeric substrates for use in tissue repair has been reported (see, e.g., Atala, A. et al. 1992 *J Urol* 148:658–62; Atala, A. et al. 1993 *J Urol* 150:608–12). Cells grown in culture can be trypsinized to separate the cells, and the separated cells can be seeded on the polymeric matrix. Alternatively, cells obtained from cell culture can be lifted from a culture plate as a cell layer, and the cell layer can be directly seeded onto the polymeric matrix without prior separation of the cells.

In a preferred embodiment, at least 50 million cells are suspended in media and applied to each square centimeter of a surface of a polymeric matrix. The polymeric matrix is incubated under standard culturing conditions, such as, for example, 37° C., 5% $CO_2$, for a period of time until the cells are attached. However, it will be appreciated that the density of cells seeded onto the polymeric substrate can be varied. For example, greater cell densities promote greater tissue formation by the seeded cells, while lesser densities may permit relatively greater formation of tissue by cells infiltrating the graft from the host. Other seeding techniques may also be used depending on the polymeric matrix and the cells. For example, the cells may be applied to the polymeric matrix by vacuum filtration. Selection of cell types, and seeding of cells onto a polymeric matrix, will be routine to one of ordinary skill in the art in light of the teachings herein.

Grafting of polymeric matrixes to an organ or tissue to be augmented can be performed according to art-recognized methods.

The techniques of the invention may also be used to treat cancer of the bladder. For example, a normal bladder tissue sample may be excised from a patient suffering from bladder cancer. Cancer treatment may involve excision of the cancerous part of the bladder in addition to chemotherapy or radiation treatment. After the cancer treatment, the RUG may be used to reconstruct the bladder.

Other methods for attaching a graft to an organ or tissue of the subject (e.g., by use of surgical staples) may also be employed. Such surgical procedures can be performed by one of ordinary skill in the art according to known procedures.

As a result of these benefits, the present method of bladder reconstructive surgery is suitable for bladder tissue repair under numerous circumstances. As described above the bladder graft may be used to repair a deteriorated bladder.

Further Description

Under the invention, the terms "cell culture" and "tissue culture" may be used interchangeably and denote the maintenance of cells in vitro, in suspension culture in a liquid medium or on surface such as glass, plastic or agar provided with liquid medium. In general, "cell culture" necessitates a medium that is buffered to maintain a constant suitable pH. Media used in cell culture are generally formulated to include an adequate supply of necessary nutrients and can be osmotically tailored to the particular cells being maintained, with temperature and gas phase also being controlled within suitable limits. Cell culture techniques are well known in the art. See, e.g., Morgan et al. 1993 Animal Cell Culture, BIOS Scientific Publishers, Oxford, UK; and Adams, R. L. P. 1990 Cell Culture for Biochemists, Second Edition, Elsevier.

The term "co-culture" is used herein to refer to a cell culture system wherein a population of cells, termed "feeder cells," is established in a cell culture in order to facilitate the proliferation of a subsequently added cell population of interest. Feeder cells can be previously irradiated or otherwise treated to prevent their division in the culture. Not being limited by any particular theory, mechanisms by which feeder cells assist in the proliferation of the cells of interest include: metabolic cooperation, wherein nucleotides, nutrients and hormonal moieties such as growth factors are passed to the cell culture via gap junctions; digestion of potentially toxic cell debris; provision of initial stimulus to cells via cell-cell contact; or combinations thereof. Cell-cell interactions can occur by direct cell-cell contact such as tight junctions, gap junctions, adherens and desmosomes. Under the invention, non-fibroblast cells, either syngeneic, allogeneic or xenogeneic, are used as feeder cells to maintain an epithelial cell culture.

The term "epithelial cell" is used herein to denote differentiated cells derived from epithelial tissue such as tissue of bladder or another luminal organ.

Major epithelial cell types include basal, luminal and myoepithelial cells and are isolated from the continuous layers of cells forming both internal and external tissue surfaces. Epithelial cells derive from both the ectodermal and endodermal embryonic cell layers.

The terms "fibroblast" and "fibroblast cell" denote a type of stellate connective cell found in fibrous tissue that is responsible for collagen synthesis in cartilage, tendon, cornea, etc. Cultured fibroblast cells are adherent cells and are normally grown on glass or plastic substrates. Cultured fibroblasts have the general morphology of tissue fibroblasts (flat, elongated or triangular-shaped cells), however they are not as differentiated as true fibroblasts. Fibroblasts derive from embryonic mesoderm and the cells that grow in culture appear to be mesodermal stem cells.

As used herein the term "normal cell" intends to refer to any cell directly derived from essentially normal cells or tissue. Thus, under the invention, "normal epithelial cells" are epithelial cells which are not of tumor cell origin, are not transformed in any detectable way and have not been immortalized.

A "malignant cell" refers to a cell directly derived from cancerous cells (or tissue) which have undergone phenotypic transformation, such as but not limited to, transformation by oncogenes, protooncogenes, TS mutations, or by other such mechanisms. "Malignant cells" are generally characterized by their capacity for invasive, unregulated proliferation. Such cells have one or more phenotypic derangements which can be expressed as alterations in cellular membranes, in the levels of certain cellular enzymes (e.g., enzymes involved in nucleic acid synthesis and metabolism), or by the appearance of inappropriate gene products.

As used herein, the term "primary culture" refers to a culture of cells that are directly derived from cells or tissue taken from an organism without intermediate culture. The cells or tissue from which a primary culture is derived is termed an explant. Cells are generally considered to be "primary cells" until they are subcultured. "Primary cells" will grow for a variable but finite length of time in culture, after which time they senesce and eventually die. Under the invention, primary cultures can be derived from a variety of tissue sources and a number of techniques for their isolation from human tissue are known in the art.

"Passage" refers to the act of subculturing a cell population. A "subculture" intends to refer to a cell culture established by the inoculation of fresh sterile medium with a sample from a previous culture. Each repeated subculture is counted as one passaging event.

A "cell strain" is a population of cells derived from a primary culture using subcultivation techniques. Thus, a primary culture can be subcultured into two or more new cultures and the subculturing repeated at periodic intervals for several months to maintain the cell strain.

A "cell line" refers to a population of cells derived from a single explant which are characterized as having the potential for unlimited proliferation in vitro. Under the invention, a cell line can be isolated from a primary culture based on its ability to survive and continue to grow in culture. Cell lines are frequently aneuploid due to an in vitro transformation event, and the capacity of cell lines to grow and divide indefinitely in culture is generally associated with an aneuploid karyotype. Cell lines which have been derived originally from tumor tissue may have been transformed in vivo, although not all neoplastic cell populations have the capacity to grow indefinitely in vitro. Further, cell lines generally retain their differentiated character through many rounds of division.

In one embodiment of the invention, a novel method of establishing a primary culture of human epithelial cells using a non-fibroblast co-culture system is provided. A sample taken from a bladder or other luminal organ is initially treated to isolate epithelial cell clumps substantially free of stromal and other cellular material. Treatment of the tissue sample to remove epithelial cell clumps from the stromal matrix and other tissue cells involves physical separation techniques such as laceration and scraping, enzymatic separation techniques such as using a digestion medium containing proteolytic enzymes, and combinations thereof.

A feeder cell population is initiated by plating a population of non-fibroblasts onto a suitable substrate and growing those cells in a tissue culture medium under suitable tissue culture conditions. The feeder cells can be selected from an established cell line of human or animal epithelial cells such as, but not limited to cell types LA7 rat mammary cells or other epithelial cells with which the cultured epithelial cells form cell-cell interactions.

Suitable cell culture substrates are generally a container that can be sterilized, does not leach toxic factors and does not distort microscopy images. Thus plates formed from glass and plastic are suitable substrates under the invention. Plastic containers may further be treated to encourage cell attachment using techniques known in the art (Ramsey et al. 1984 In vitro 20:802). Suitable tissue culture media generally consist of an isotonic, buffered, basal nutrient medium which provides an energy source, coupled with inorganic salts, amino acids, vitamins and various supplements. Supplements may include serum (e.g., fetal calf serum, or the like) various antibiotics to prevent contamination or to provide selective conditions, attachment and growth factors, or the like. A number of media formulations are known in the art, such as, but not limited to, minimal essential medium (MEM), Rosewell Park Memorial Institute (RPMI) 1640 or Dulbecco's modified Eagle's medium (DMEM). Suitable tissue culture conditions are also known in the art. See, e.g., Morgan et al. 1993 Animal Cell Culture, BIOS Scientific Publishers Ltd., Oxford, UK, and Adams, R. L. P. 1990 Cell Culture for Biochemists, Second Edition, Elsevier.

After the non-fibroblast feeder cells have been plated as described above, and allowed to attach to the substrate, the cells are grown until the desired density is reached; usually, this is when the surface area is completely covered with cells (known as a confluent layer of cells). Monolayers may optionally be cultured to about 80% confluency, preferably to about 90% confluency, and more preferably about 100% confluency.

Feeder cells may be mitotically inactivated using standard techniques. For example, the feeder cells may be exposed to gamma radiation (e.g., 4,000 Rads of gamma radiation), or may be treated with Mitomycin C (e.g., 10 µg/ml for 2–3 hrs).

Once the isolated epithelial cell clumps are substantially freed from other tissue cells, the clumps are finely divided to provide epithelial cell clusters that are as small as possible. The cell clusters (explants) are then brought into suspension in a suitable medium and applied to the non-fibroblast feeder cells. The co-culture system thus provided is incubated under suitable tissue culture conditions. After a suitable time (generally about 2–3 days), outgrowth from the explant occurs, whereby a primary culture of human epithelial cells is formed capable of further in vitro proliferation.

Under the invention, the above described methods can be used to produce primary cultures of normal human epithelial cells derived from samples of human tissue. In like manner, primary cell culture systems derived from excised cancerous or malignant human tissue can also be produced. These systems have, for the most part, not been obtainable in the prior art, primarily due to the lack of suitable in vitro tissue culture methods for establishing well defined, malignant epithelial cells.

Once primary cultures have been obtained as described above, epithelial cells from those cultures can be passaged using tissue culture techniques known in the art. After several passages, an outgrowth of epithelial cells capable of many population doublings, and even proliferation as individual clones is obtainable.

Thus, in a further embodiment of the invention, a method is provided for passaging human epithelial cells from the primary cultures established above. In the maintenance of the primary cultures, epithelial cells are permitted to reach confluence, and then they are subcultured. Thus, when the cells approach confluence, they are passaged to a fresh co-culture system. Passaging techniques are used under the invention to obtain substantially pure epithelial cell cultures and to establish subcultures thereof.

In order to obtain a substantially pure epithelial cell culture from the primary cultures initiated above, a fresh culture of non-fibroblast feeder cells is established using techniques as previously described. The feeder cells are allowed to adhere to the fresh substrate and grow to confluency and are then lethally treated. In this regard, it is generally preferable to use the same non-fibroblast line with which the co-culture system was started.

Subculturing under the invention can be carried out using established tissue culture techniques. Epithelial cells are detached using techniques known in the art. At this point, the cells may be counted and known populations seeded onto a fresh non-fibroblast feeder culture to provide epithelial cell strains.

In yet a further embodiment of the invention, epithelial cell strains derived from human tissue are immortalized to provide cell lines. The use of transfection techniques to introduce "immortalization genes" into primary cells in vitro has been described in the art. These techniques allow cells to proliferate as immortal cell lines without suffering a concomitant loss of function. Use of immortalized cells constructed under the invention in, for example, cancer research avoids the problems associated with having to use cell lines derived from malignant tissue which express a transformed phenotype.

Under the invention, the primary cell cultures, passaged cell strains, and immortalized cell lines can be characterized by their expression of specific functional markers such as keratins, hormonal and growth factor receptors and the like. Particularly, human bladder epithelial cells may be phenotypically characterized by their expression of keratins 7, 10, 11, 18 and 19, and ZO1 tight junction protein but not vimentin or keratin 14, using immunoaffinity and detection techniques known in the art.

Thus, monoclonal antibodies specific for a selected cell marker (or a second antibody directed against the monoclonal antibody), can be labeled with a suitable detectable chemical group, such as an enzyme, radioisotope, fluorescer, chromophore, luminescer or ligand for rapid and sensitive detection using techniques known in the art. Depending on the nature of the label, a number of techniques to detect the presence of the label are known, e.g., fluorometric, spectrophotometric, autoradiography, scintillation counting, and visual (e.g., colorimetric or chemiluminescence) techniques.

Other selected phenotypic markers, or fragments thereof, can be used as an antigen to produce antibodies, either polyclonal, monoclonal, or both, by methods which are well known in the art. If polyclonal antibodies are desired, a selected mammal, (e.g., mouse, rabbit, goat, horse, pig, etc.) is immunized with a selected antigen or a fragment thereof. Serum from the immunized animal is collected and treated according to known procedures. If serum containing polyclonal antibodies is used, the polyclonal antibodies can be purified by immunoaffinity chromatography, using known procedures.

Monoclonal antibodies to a selected cell marker can also be readily produced by one skilled in the art. The general methodology for making monoclonal antibodies using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500; 4,491,632; and 4,493,890.

The human epithelial cell cultures of the invention can be used in the context of in vitro assays to screen for potential carcinogens. Epithelial cells provide a useful model system in carcinogen testing since they mimic more closely the usual situation in humans and animals, where carcinomas are typically derived from epithelial, not mesenchymal cells. Epithelial cell cultures of normal or precancerous phenotypes that are produced using the co-culture system of the present invention can be plated, allowed to adjust, and a portion thereof exposed to an agent suspected of being a carcinogen for a suitable period of time. Exposure to the agent is terminated by removal of culture media containing the agent, washing with a suitable buffered wash solution and adding fresh growth media.

Transformation events which occur as a consequence of exposure to the agent can be identified by development of foci of transformed cells. Alternatively, transformation events can be monitored by injection of treated cells (either subcutaneously or intraperitoneally), into immunocompromised animal models (e.g., nude or SCID mice), wherein the ability of the treated cells to form solid tumors can be readily ascertained.

Additional Description

The present invention provides an in vitro human bladder epithelial system that is capable of proliferation for many generations. Moreover, the in vitro human bladder epithelial system of the present invention forms multilayers covered by umbrella cells and expresses keratins characteristic of in vivo human bladder epithelial cells.

Specifically, the advantages of the present system for culturing epithelial cells are that both normal and malignant cells can be grown, the cells can multiply for many generations, the cells can be cloned, cultures of normal cells include multilayers and differentiated umbrella cells as they would in vivo, fibroblast overgrowth never occurs, and that normal complements of intermediate filaments are expressed. Cultures derived by the present method may be used to study the physiology of normal bladder epithelium or characteristics of various tumors. In addition, the methods or compositions of matter of the present invention, or derivatives thereof, may be used for implants or components of implants for artificial bladders in human patients.

Unlike the stimuli used to promote epithelial cell proliferation in prior culture systems, growth stimulation in the system of the present invention is achieved, not by growth factors added to the culture medium or secreted by fibroblast cells, but rather by direct, contact stimulation of the human bladder epithelial cells by adjacent epithelial cells of the same or another type. In the present invention, non-proliferating epithelial cells are used to stimulate the proliferation of the human bladder epithelial cells. The non-proliferating epithelial cells may be irradiated epithelial cells, for example. The method may be used as an in vitro model of epithelial tissue. Epithelial cells, unlike other cell types such as fibroblasts, are connected on all sides to other similar cells in vivo. Epithelial cells form an intact barrier to specific ions, molecules, and solutes by forming tight junctions between each cell. The integrity of this barrier must be maintained even when a cell within the tissue dies. In fact, some signal(s) must be transmitted to stimulate the healthy cells to divide when a damaged cell is lost from the confluent epithelial tissue. Thus, in the present invention, the original confluent monolayer of non-proliferating epithelial feeder cells and human bladder epithelial cells transforms into a multilayered confluent culture of human bladder epithelial cells.

The culture method of the present invention was originally developed for mouse mammary epithelial cells. Cells of the LA7 rat mammary line (ATCC # CRL-2283) were chosen as feeders that the mouse mammary epithelial cells might recognize as being similar, and with which the mouse mammary epithelial cells might form a demi-epithelial tissue in vitro if the two cell types were plated together at a confluent density. Indeed, as the lethally irradiated feeder cells slowly died, the mouse mammary cells divided to occupy the spaces of the dying feeders. In this way the confluent monolayer slowly changed from one composed mostly of feeder cells to one composed entirely of mouse mammary cells (see, Ehmann, U. K. et al. 1984 *J Cell Biol* 98:1026).

Since soluble growth factors do not appear to be involved in the stimulus to proliferate in the culture system of the present invention, it is likely that the success of this method depends on stimulation by membrane bound growth factors and/or the formation of physical junctions between the feeder cells and the epithelial cells. For example, mouse mammary cells form several types of junctional complexes with the rat LA7 feeder cells (see, Ehmann, U. K. et al. 1998 *Exp Cell Res* 243:76), suggesting that membrane-bound growth factors and physical junctions necessary for proliferation stimulation may be similar in some different tissues and in some tissues of different species.

Thus, a novel feature of the present human bladder epithelial cell system is that cell proliferation is induced by non-proliferating epithelial cells rather than by growth factors added to the medium or fibroblast feeder cells. The inability of LA7 rat epithelial cell-conditioned medium to stimulate human bladder epithelial cell proliferation indicates that these feeders are not releasing the necessary growth stimulatory factors into the medium. Instead, the requirement that the mixed LA7/human bladder epithelial cell culture be confluent for human bladder epithelial cell proliferation to occur strongly indicates a direct cell-cell contact mechanism of growth signal transmission.

The use of fibroblast cells as feeders, a fairly common practice in the culture of various epithelial cells, differs in significant ways from the present use of epithelial feeders. Fibroblast feeders are usually plated at a low density, in contrast to the LA7 feeders in the present invention, which are plated at a confluent density. The low density of fibroblasts used for feeder layers generally minimizes the formation of junctions between the fibroblasts and the epithelial cells, indicating that the observed growth stimulation in the epithelial cells is stimulated by molecules that the fibroblasts secrete into the medium, not cell to cell contact. The proliferative stimuli from LA7 feeders, on the other hand, are not transmitted to the human bladder epithelial cells by substances secreted into the medium, as LA7 conditioned medium does not stimulate human bladder epithelial cell proliferation.

That human bladder epithelial cells can be stimulated by neighboring human bladder epithelial cells was shown by others who identified heparin-binding epidermal growth factor (HB-EGF) as a stimulatory molecule produced by human bladder epithelial cells and ErbB1 as the receptor on human bladder epithelial cells for that ligand. ErbB1 is stimulated by a family of growth factors including Transforming Growth Factor α (TGF-α), which is active in its transmembrane form as well as its secreted form. TGF-α is produced by the LA7 cells used in the present in the experiments of the present invention as feeders (Ehmann U. K. et al. 2003 *Cell Proliferation* 36:177–190). The fact that mechanical stretching of human bladder epithelial cells induces ErbB1 expression (see Nguyen, H. T., et al. 1999 In vitro *Cell Dev Biol.-Animal* 35:371) may also have some relevance to the present culture system, in which confluency is maintained from the time of plating a mixture of human bladder epithelial cells and feeders to the time when this culture is composed completely of human bladder epithelial cells. As a feeder cell dies, all other cells, including both human bladder epithelial cells and feeders—all connected by cell junctions—must stretch to maintain confluency of the culture. As human bladder epithelial cells are stretched, more receptors may be expressed on the cell surfaces, making the cells more responsive to TGF-α on adjacent feeder cells and to HB-EGF from neighboring human bladder epithelial cells. In the culture system of the present invention, the density requirement of confluency is necessary for cell proliferation.

The feeder cells and human bladder epithelial cells may be plated and grown in cell culture media with serum. Preferably, the serum is fetal calf serum or newborn calf serum, and is in a concentration of about 0% to about 10%. More preferably, the concentration is about 0.5% to about 5%. Cell culture media known in the art may be used. For example, Dulbecco's Modified Eagle Medium mixed with Ham's F12 medium was used in the experiments of the present invention. However, one skilled in the art would know to choose any cell culture medium appropriate for the cell type being cultured. In addition, various media additives may be employed as well, including antibiotics, hormones, growth factors, nutritional supplements, vitamins, minerals and the like.

In some aspects, cultures in serum-free defined media with added growth factors have advantages over the present culture system. For example, these culture systems offer defined medium composition, generally a more rapid cell proliferation, and are not complicated by the presence of another cell type. Several investigative groups have successfully cultured various epithelial cells of both human and animal origin in defined media without feeder cells, achieving lifespans of twenty or more generations. Some bladder cultures in defined media with growth factors have also been shown to express various characteristics of normal bladder tissue, such as presence of keratins 7, 18, or 19, multilayering of cells, formation of various junctions between cells, or diploid karyotypes. However, cultures in defined media have lacked certain features of well-differentiated bladder cells, namely, the presence of a superficial layer of umbrella cells with an asymmetrically thickened plasma membrane. Moreover, expression of keratin 14 and vimentin—filaments not usually associated with normal transitional bladder epithelial cells in vivo—also have been reported to be expressed in bladder cells cultured in defined media.

The culture method of the present invention, in contrast, can perpetuate both normal cells and cells from some malignant tumors for more than 20 generations, promote development of a superficial umbrella layer of large cells connected by tight junctions, and promote growth of clones from single cells from bladder washes. In addition, the human bladder epithelial cells cultured by the present method express not only the appropriate keratins for transitional epithelial cells, but do not express detectable keratin 14 or vimentin. These traits characteristic of differentiated in vivo epithelial tissue were retained into advanced passages of the normal human bladder epithelial cells in the present culture system.

The methods and compositions of the present invention may be used as in vitro systems to study the physiology of normal bladder epithelium or of tumors derived from the bladder epithelium. For example, the in vitro bladder epithelial system of the present invention might be used in assays for agonists or antagonists of epithelial cell proliferation, epithelial cell-cell communication, epithelial cell contact inhibition, or ion transport across cell membranes. Further, the methods and compositions of the present invention may be used as implants or components of implants for bladder repair or reconstruction in humans. For example, the cultured human bladder epithelial cells of the present invention may be used to repopulate an acellular matrix, such as those sold by LifeCell Corp. (Branchburg, N.J.) under the trademarks Repliform, Alloderm and Cymetra for bladder repair. Alternatively, the cultured human bladder epithelial cells of the present invention may be used on their own without additional components in bladder repair or reconstruction.

EXAMPLE 1

Bladder Tissue Acquisition and Preparation

To assess the ability for proliferation of cells from bladder washes, bladder wash samples taken for diagnostic purposes were centrifuged, and the cells were then resuspended in tissue culture medium and plated with a monolayer of lethally irradiated (60 Gray) LA7 cells. The co-cultures were fed three times a week. On the eighth day after plating, areas of each flask that contained a colony were encircled with a diamond needle and photographed. Each colony was rephotographed on day 20. The relative area of each colony was determined by cutting out the image of the colony traced onto plastic cellophane and weighing it.

Surgical tissue for the cultures of the present invention was harvested from fresh human bladder specimens removed during radical cystectomy for transitional cell carcinoma or during bladder resection as part of urinary reconstructive procedures. After the tissue specimen was rinsed three times in phosphate-buffered saline (PBS), it was chopped into small segments with a single-edged razor blade and inserted into collagen-I coated tissue culture flasks.

EXAMPLE 2

Culture Conditions

In some cases the human bladder epithelial cells were plated along with the feeder LA7 cells. In other cases the human bladder epithelial cells were plated first and the feeders were added a few days later. In all cases the total number of cells was adjusted such that a confluent monolayer was achieved with a combination of the human bladder epithelial cells and LA7 cells together. To prepare subcultures, the confluent human bladder epithelial cells were dislodged from the tissue culture substrate by a trypsin-EDTA PBS solution and introduced into a new flask at the desired dilution, usually 1:5–1:20, from which the human epithelial bladder cells would again proliferate to cover the flask surface, as long as fresh feeder cells were provided at a concentration to achieve confluence. For the immunocytochemistry experiments, T25 flasks of confluent irradiated feeder cells were inoculated with approximately 3000 human bladder epithelial cells each and fed regularly until colonies appeared within the feeder bed. Primary and secondary cultures were plated into flasks coated with Vitrogen 100 (Celtrix Laboratories (Palo Alto, Calif.)) (Vitrogen 100 is mostly collagen I). Advanced passages were plated onto uncoated tissue culture plastic.

The cells were cultured in a 1:1 combination of Dulbecco's modified Eagle's medium and Ham's F12 medium (Hazleton Biologics, Lenexa, Kans.) supplemented with 5–10 µg/ml insulin, 5 µg/ml transferrin, 0.2 mM (120 U/ml) penicillin G, 0.05 mM streptomycin sulfate (Sigma Chemical Co., St. Louis, Mo.), 20 mM HEPES buffer, 2.0 g/l $NaHCO_3$, 0.5 or 5% fetal bovine serum (Sterile Systems, Logan, Utah) or newborn calf serum (Sigma Chemical Co.), and a supplement of trace minerals including selenium, copper, manganese, silicon, molybdenum, vanadium, tin, and zinc. The cells were fed with fresh medium three times per week.

EXAMPLE 3

Feeder Cells

Rat mammary cells of the LA7 line are a clonal derivative of the Rama 25 line which came from a Sprague-Dawley rat treated with dimethylbenz(a)-anthracene (see Dulbecco, R., et al. 1979 *PNAS USA* 76:1256). The LA7 cells were regularly cultured on tissue culture plastic in DMEM:F12 (1:1) supplemented with 20 mM HEPES buffer, 2.0 g/l $NaHCO_3$, 5–10% fetal or newborn bovine serum, antibiotics, 5–10 µg/ml insulin, and 50 nM hydrocortisone. Before plating with the epithelial cells, the LA7 cells were proliferatively inactivated by a single dose of 60 Gy (6,000 rads) from a $^{137}CS$ source.

EXAMPLE 4

Measurement of Growth Rate

Human bladder epithelial cells were dislodged from confluent culture by trypsin-EDTA dissociation and plated at approximately $1 \times 10^5$ human bladder epithelial cells per 35-mm Petri dish, either with or without feeders. On the day of the count, the cells were dislodged by trypsin-EDTA, diluted into 20 ml medium with 5–10% serum, and pulled through a 23 gauge needle to break the cell clumps into a single cell suspension. Two milliliters of this suspension were diluted and counted on a ZBI Coulter counter (Coulter Electronics, Hialeah, Fla.). The remaining cells were aggregated into a pellet by centrifugation. An FITC conjugated mouse anti-rat MHC class I antibody (Pharmingen, San Diego, Calif.) was added to the cell pellet at a dilution of 1:4. After incubation at 37° C. for 1.5 hours, PBS was added to rinse the cell mixture, and the cells were again aggregated by centrifugation. The cells were preserved in 1 ml of 1% paraformaldehyde in PBS at 4° C. until the day of analysis on a Becton-Dickinson FACScan (San Jose, Calif.). The Cellquest software program sorted 20,000 cells per sample according to fluorescence intensity.

EXAMPLE 5

Immunocytochemistry

Cells were cultured in 25 $cm^2$ tissue culture flasks until the cultures were mature for study, i.e., either confluent human bladder epithelial cells or colonies of human bladder epithelial cells surrounded by feeders. The cultures were fixed in 1% paraformaldehyde at room temperature or methanol at −80° C. for 20–30 minutes and then covered with PBS containing sodium azide for storage at 4° C. until the day of the experiment. The cells were permeabilized with 0.5% triton-X 100 in Hank's BSS for 20 minutes and rinsed with PBS. A first stage antibody (see Table 1) or a control pre-immune serum was applied to part of the culture flask, which was then incubated at 37° C. for about 1.5 hours. After rinsing, a second stage antibody (see Table 1) conjugated with fluorescein was applied and incubation proceeded at 37° C. for approximately one hour. After rinsing, the coverslip was mounted over a solution of 2.5% 1,4 diazobycyclo[2.2.2]octane (Fluka Chemika, Ronkonkoma, N.Y.) as a fluorescence saver and 90% glycerol in PBS. Cells were viewed on an inverted Nikon Diaphot microscope equipped with epifluorescence, and photographs were taken with a Nikon 35-mm N2000 camera and 400 ASA black and white film.

TABLE 1

ANTIBODIES

| | First Antibody | | | Second Antibody | | |
|---|---|---|---|---|---|---|
| Antigen | Source* | dilution | Vendor | Source | dilution | Vendor |
| Keratin 7 | Mouse m | 1:100 | Sigma | Horse FITC | 1:100 | Vector |
| Keratins 10, 11 | Mouse m | 1:20 | Sigma | Horse FITC | 1:100 | Vector |
| Keratin 14 | Mouse m | 1:30 | Neomarkers | Horse FITC | 1:100 | Vector |
| | Mouse m | 1:200 | Sigma | Goat FITC | 1:150 | Sigma |
| Keratin 18 | Mouse m | 1:50 | Sigma | Horse FITC | 1:100 | Vector |
| Keratin 19 | Mouse m | 1:30 | Neomarkers | Horse FITC | 1:100 | Vector |
| Vimentin | Mouse m | 1:30 | Sigma | Horse FITC | 1:100 | Vector |
| Uroplakin III | Mouse m | none | Research Diagnostics | Horse FITC | 1:100 | Vector |
| Z01 Protein | Rabbit p | 1:50 | Zymed | Goat FITC | 1:100 | Sigma |

*m, monoclonal; p, polyclonal

EXAMPLE 6

Fluorescence In Situ Hybridization

Normal human bladder epithelial cells frozen after confluency in passages 1 and 6 and human bladder epithelial cells from a tumor frozen after confluency in passages 2 and 5 were thawed, rinsed twice in PBS, and centrifuged into a pellet. The pellets were suspended in 7 ml fixative of 3:1 methanol:acetic acid with gentle agitation and frozen at −20° C. overnight. The next morning the cells were centrifuged and resuspended in fresh fixative 3×. Then 3–30 µl of cell suspension were dropped onto slides and allowed to air dry. The hybridization procedures of Vysis (Downers Grove, Ill.), who supplied the equipment and reagents for this procedure, were followed. Briefly, the samples were digested by a protease solution, fixed in 1% formaldehyde, and dehydrated in ethanol. The UroVysion Multicolor Probe to chromosomes 3, 7, 17, and 9 were added and the samples were melted in a hybridization chamber for 2 minutes at 73° C. after which hybridization was carried out at 39° C. for 4 hours. After hybridization, the slides were incubated at 73° C. in buffer with 0.1% NP-40 and dried. A solution of DAPI II was dropped onto them. The slides were then viewed on an epifluorescent microscope with appropriate filters to detect red, green, aqua, and gold fluorescent spots on the hybridized chromosomes. The number of spots of each color was counted for cells in each sample.

EXAMPLE 7

Results

Figure 1:
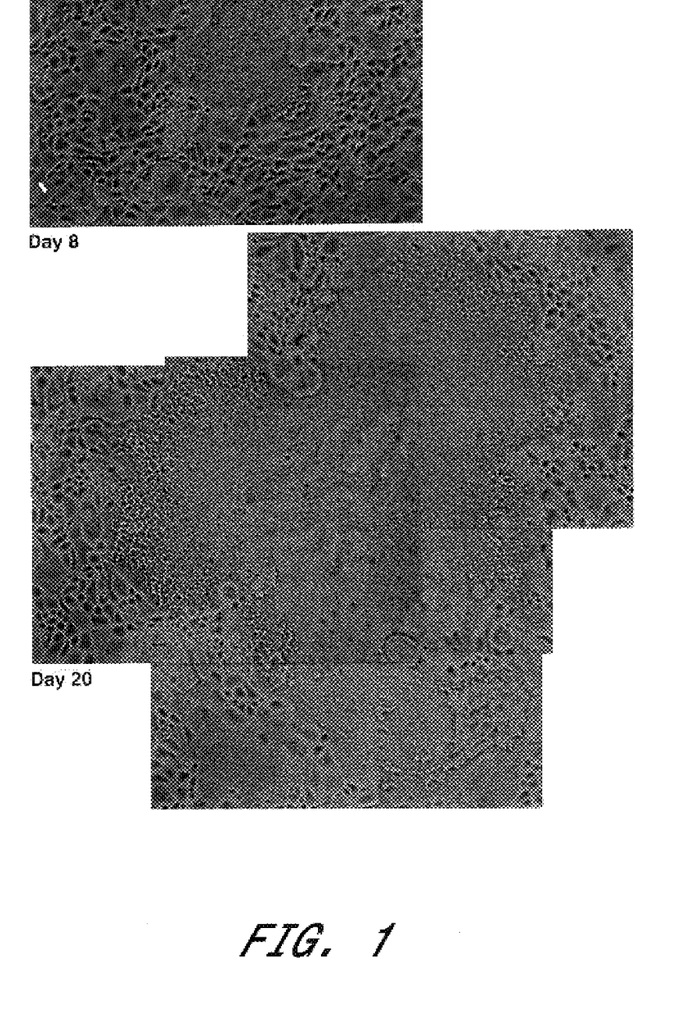
FIG. 1 shows a colony of human bladder epithelial cells that grew from one or a small number of cells from a patient bladder wash.

In the present invention, cells from bladder washes formed colonies after being plated with a confluent monolayer of lethally irradiated LA7 feeder cells. No human bladder epithelial cells were visible at the time of plating or for the first few days, suggesting that the plated cells were singlets or in small groups. After eight days small colonies had arisen amongst the feeder cells in cultures from all three patients (see FIG. 1 and Table 2). After twenty days all colonies had increased in size from factors of approximately 4 to 16 times their sizes on day eight (again, see FIG. 1 and Table 2). FIG. 1 shows a colony of human bladder epithelial cells that grew from a bladder wash. Colony #2 from patient C in Table 2 was photographed on days 8 and 20 after the cells from the bladder wash were plated with lethally irradiated LA7 feeder cells. The photo on day 20 is a composite to encompass the periphery of the colony. LA7 feeder cells surround the colony in both photographs. The magnification is 100×.

TABLE 2

COLONIES FROM BLADDER WASHES

| | | Area of colony (in mg cellophane) | | Colony growth |
|---|---|---|---|---|
| Patient No. | Colony No. | day 8 | day 20 | day 20/day 8 |
| 1 Bladder Carcinoma | 1 | 33 | 319 | 9.7 |
| | 2 | 33 | 135 | 4.1 |
| 2 Bladder Carcinoma | 1 | 30 | 471 | 15.7 |
| | 2 | 56 | 606 | 10.8 |
| 3 Normal Bladder | 1 | 27 | 420 | 15.6 |
| | 2 (FIG. 1) | 84 | 934 | 11.1 |
| | 3 | 160 | 753 | 4.7 |

Human bladder epithelial cells from normal and malignant surgical specimens also proliferated when plated with irradiated LA7 cells at a confluent density. Cells from five normal bladder tissues adapted easily to tissue culture. The human bladder epithelial cells multiplied to displace dying feeder cells until the entire culture became confluent with human bladder epithelial cells. These human bladder epithelial cells could then be diluted and subcultured by being mixed with fresh, irradiated LA7 cells and replated at a confluent density. Human bladder epithelial cells from one of the normal tissues was carried to confluency in passage eleven, amounting to at least 37 cell doublings in culture. At the time of termination of the passages, the growth rate of the cultures from all five normal tissues had not diminished, and there were no other signs of senescence.

Figure 2:
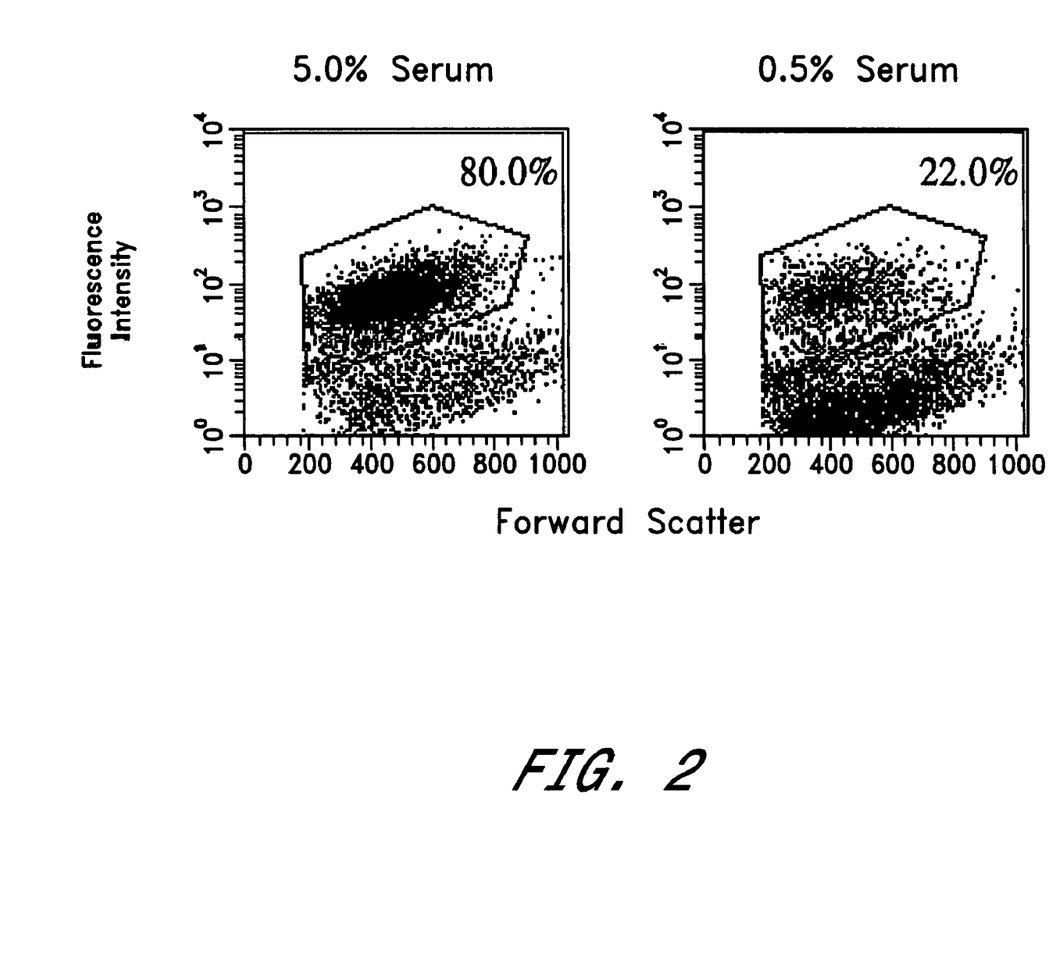
FIG. 2 shows a FACScan analysis of percentages of LA7 feeder cells in co-culture with human bladder epithelial cells on day 20 after plating the two cell types together.
Figure 3:
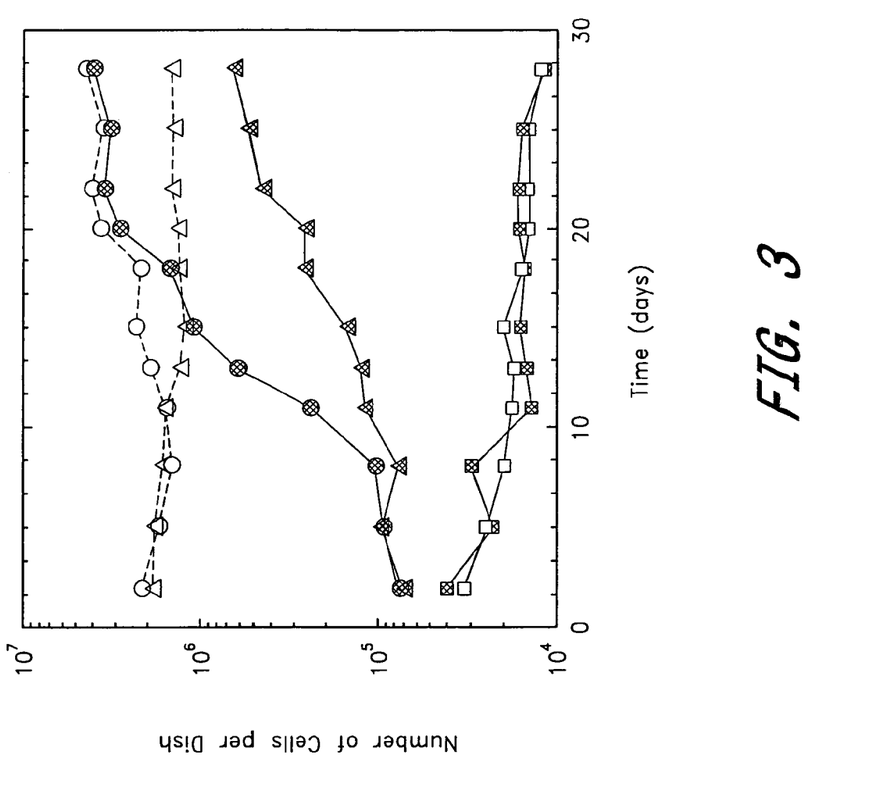
FIG. 3 shows proliferation of normal bladder epithelial cells in passage 4. It shows that medium conditioned by LA7 cells does not stimulate proliferation of bladder cells, whereas direct contact of bladder cells with LA7 cells does stimulate proliferation. It shows that bladder cells proliferate more rapidly with low (0.5%) serum concentrations than with high (5.0%) concentrations.

Normal human bladder epithelial cells in passage 4 cultured in the methods of the present invention doubled in number in about two days when cultured in medium with 0.5% serum, and in 5.6 days in medium with 5.0% serum (see FIGS. 2 and 3). FIG. 2 shows a FACscan analysis of percentages of LA7 feeder cells in co-culture with human bladder epithelial cells on day 20 after plating. Polygons define populations of irradiated LA7 feeder cells, i.e., those that reacted with an FITC-conjugated anti-rat antibody. Of the cells cultured in 5.0% serum, 80.0% were LA7 feeders whereas of cells cultured in 0.5% serum, 22.0% were LA7 cells.

FIG. 3 shows proliferation of normal human bladder epithelial cells in passage 4. All points were obtained by analyses similar to those in FIG. 2. The bladder epithelial cells cultured in the methods of the present invention doubled in number in about two days when cultured in medium with 0.5% serum, and in 5.6 days in medium with 5.0% serum (see FIGS. 2 and 3). (o) total number of co-cultured human bladder epithelial cells and LA7 feeders in medium with 0.5% serum; (●) number of human bladder epithelial cells only, in co-culture with LA7 cells in 0.5% serum; (Δ) total number of co-cultured human bladder epithelial cells and LA7 feeders in medium with 5.0% serum; (▲) number of human bladder epithelial cells only, in co-culture with LA7 cells in 5% serum; (■) number of human bladder epithelial cells cultured alone with fresh medium; (□) number of human bladder epithelial cells cultured alone with ½ fresh+½ LA7-conditioned medium. FIG. 3 shows that culture medium conditioned by LA7 cells does not promote proliferation of the bladder epithelial cells. Only the bladder cells in direct contact with the LA7 cells proliferated. Therefore the growth stimulus provided by the LA7 cells is not a secreted factor.

Human bladder epithelial cells plated without feeders did not proliferate at all whether the medium was fresh or partly conditioned by LA7 feeders (again, see FIG. 3). In fact, the numbers of human bladder epithelial cells declined if they were plated alone. The plating efficiency of cells plated with feeders in the experiment on which FIG. 3 reports was virtually 100%, whereas only half as many cells survived trypsinization and transfer when they were plated alone. The cloning efficiency of human bladder epithelial cells in passage five was approximately 9%, as compared to the usual 100% plating efficiency. The lower cloning efficiency is most likely due to cell injury caused by the cells having been drawn through a needle as was done to break up the clumps into single cells before plating.

Figure 4:
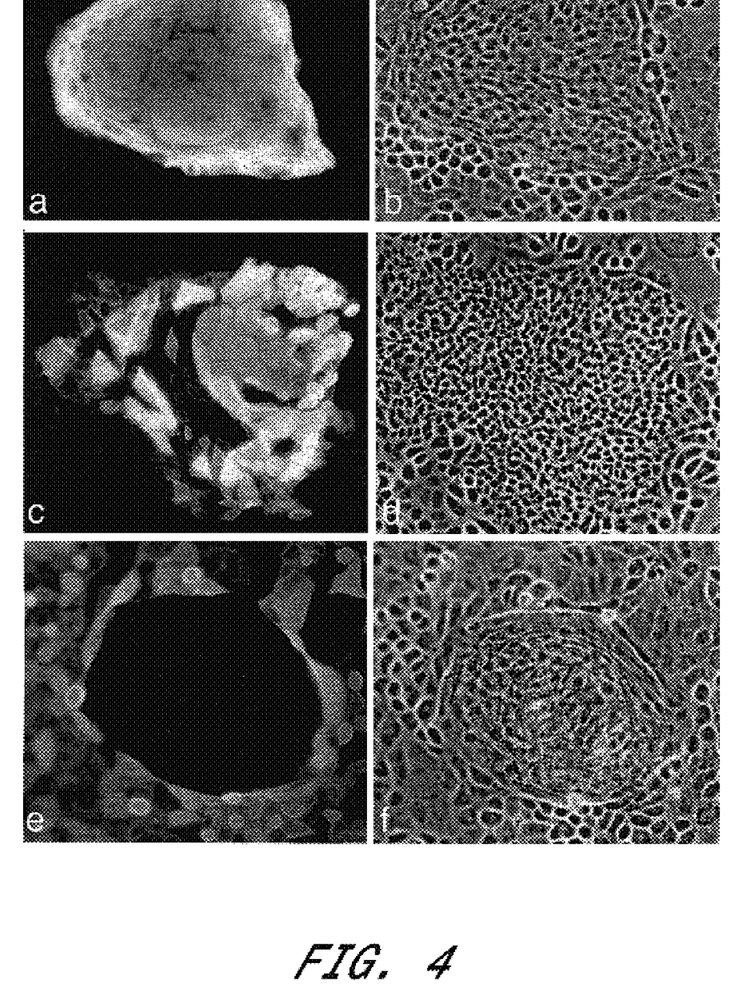
Figure 5:
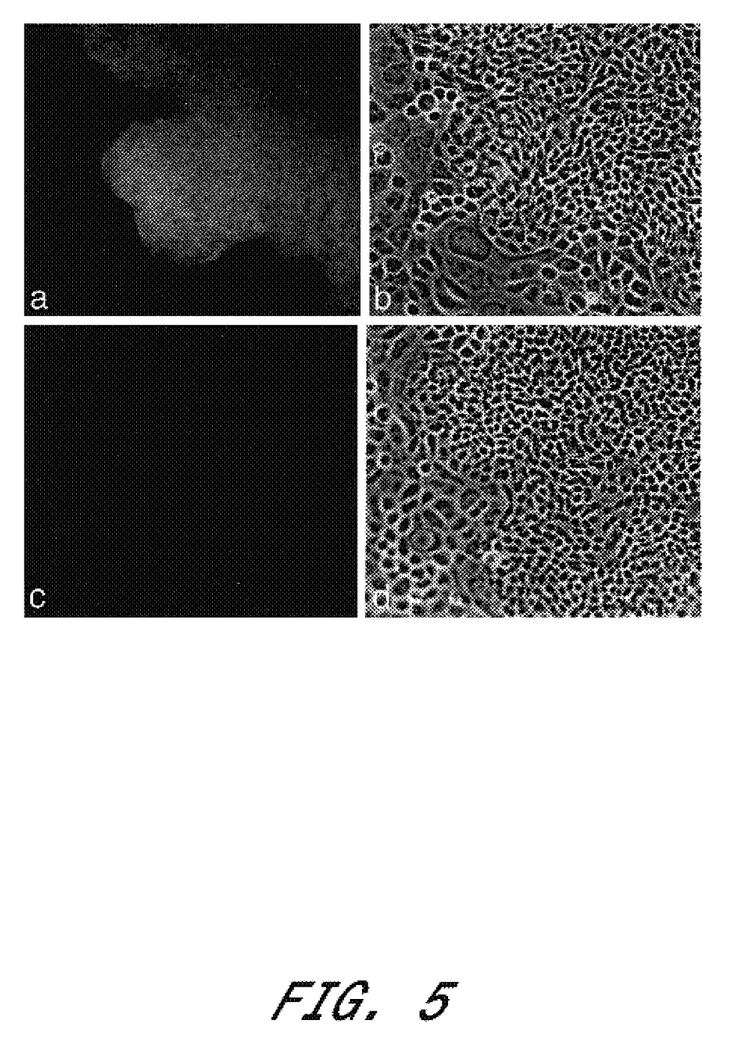

Normal human bladder epithelial cells strongly expressed keratins 7, 10, 11, 18, and 19, but did not express keratin 14 or vimentin (FIGS. 4, 5, and Table 3). FIG. 4 shows normal human bladder epithelial cells in passage 6 incubated with antibodies to keratins 18, 19, and 14. (a.) An anti-keratin 18 fluorescently labeled colony of human bladder epithelial cells surrounded by LA7 feeder cells is shown. (b.) A phase contrast image of field of cells in frame (a) is shown. Note that the large stained umbrella cells in (a) are not visible in (b). (c.) An anti-keratin 19 fluorescently labeled colony of human bladder epithelial cells surrounded by feeder cells is shown. Cells of the basal layer of the colony are visible at the colony edges, and large labeled umbrella cells are visible in the colony center. (d.) A phase contrast image of the field of cells in frame (c) is shown. The umbrella cells of frame (c) are not visible in this image. (e.) Anti-keratin 14 fluorescently labeled cells are shown. Note that the human bladder epithelial cell colony in the center did not react with the antibody, but the surrounding LA7 feeder cells did. (f.) A phase contrast image of cells in field (e) is shown. See frames (c) and (d) of FIG. 5 for the pre-immune control. Magnification is at 100×.

FIG. 5 shows normal human bladder epithelial cells in passage 6 incubated with an antibody to keratin 7. (a.) The human bladder epithelial cell colony shines with the fluorescently labeled antibody, but the surrounding feeder cells do not. (b.) A phase contrast image of field of cells in (a) is shown. (c.) A fluorescent image of control cells incubated with a pre-immune mouse serum is shown. (d.) A phase contrast image of field of cells in frame (c) is shown. Magnification is at 100×.

TABLE 3

| | | | ANTIGEN EXPRESSION | | | | | | |
|---|---|---|---|---|---|---|---|---|---|
| CELLS | K7 | K10, 11 | K14 (Neo-marker) | K14 (Sigma) | K18 | K19 | Uroplakin III | Vimentin | Z01 |
| Normal | +++½ | ++½ | – | – | +++ | ++++ | +++ | – | +++½ |
| Tumor | +++ | ++ | – | N.D. | +++½ | ++++ | +++ | – | ++++ |
| LA7 (feeder) | – | ++ | +++ | +½ | – | – | +++ | +++ | +++½ |

From no staining (–) to maximum staining (++++)
N.D.: not done

Figure 6:
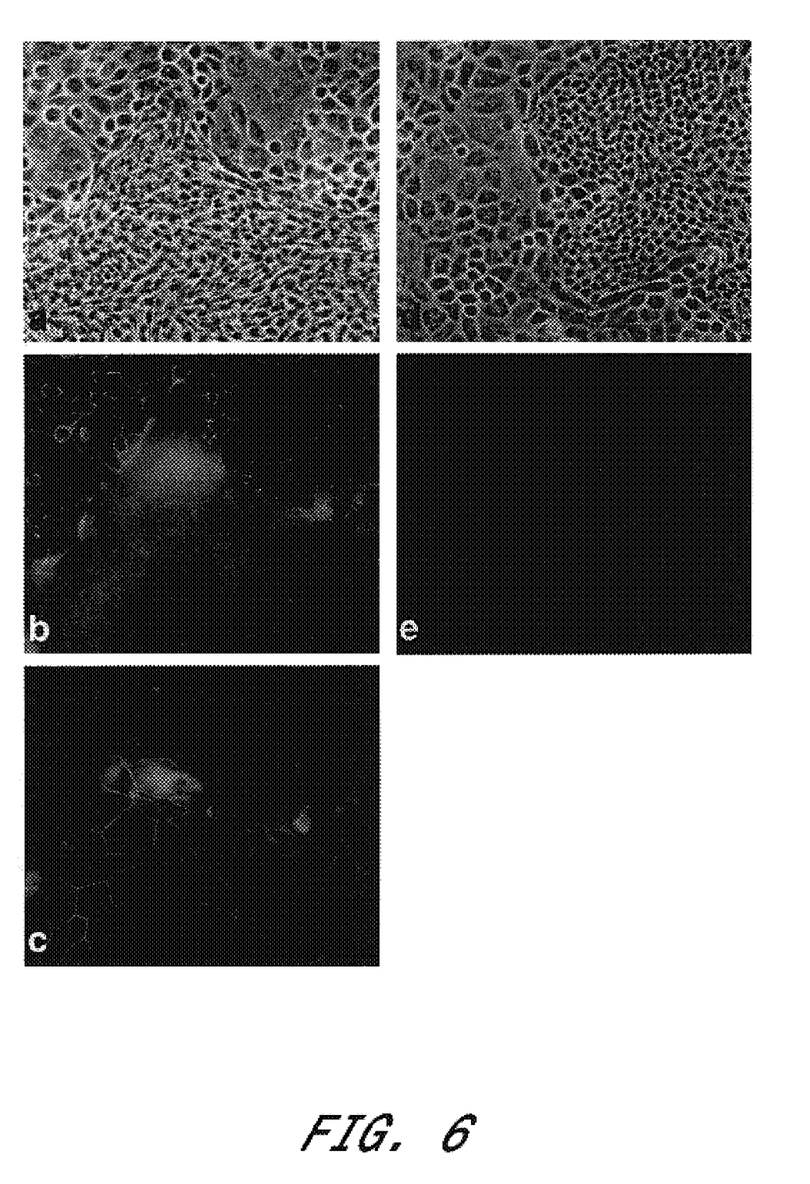

The areas of cell colonies studied appeared by phase microscopy to consist of a single layer, but after fluorescent labeling with antibodies to some of the keratins, a superficial layer of very large "umbrella" cells became visible (again, see FIG. 4). Cells of this umbrella layer connected to each other and also to the feeder cells by tight junctions (see FIG. 6). FIG. 6 shows normal human bladder epithelial cells in passage 6 incubated with an antiserum to the ZO1 protein of tight junctions. (a.) A phase contrast image of a human bladder epithelial cell colony in the lower part of the photograph with LA7 feeders above is shown. (b.) The fluorescent image of the ZO1 protein at cell perimeters is shown. Feeder LA7 cells are in the plane of focus. ZO1-marked cell borders are visible at the border between feeders and human bladder epithelial cells colony. (c.) A fluorescent image of ZO1 protein is shown. Cells of the human bladder epithelial cells colony are in the field of focus. The cells whose perimeters are visible are much larger than the cells of the phase contrast image of (a.) and reside in a higher plane of focus. These larger cells are the umbrella cells. (d.) A phase contrast image of human bladder epithelial cell colony on right side of the photograph with LA7 feeders to the left is shown. (e.) A fluorescent image of the cells in frame (d) treated with pre-immune control serum is shown. Magnification is at 100×.

FIG. 6 also shows that the tight junctions of the umbrella cells exist in a different plane than those of the LA7 cells, confirming that they are slightly above the basal layer of human bladder epithelial cells. The colonies depicted in FIGS. 4 and 5 were young, proliferating groups of cells. These enlarged cells began to stack upon each other, and by the time confluence was achieved, about two-thirds of the surface of the cultures was visibly multilayered. At confluence the entire culture, including areas that appeared to be a single layer by phase microscopy, were covered by a sheet of umbrella cells.

Three of four human tumor samples introduced into culture eventually became long-term cell cultures. Cultures originating from two tumors were carried through passage nine, amounting to at least 20 and 27 doublings in culture, respectively, and one strain was carried through passage six, amounting to 16 doublings. The tumor cultures differed from one other and from the normal cultures in both morphology and growth characteristics. Two of the tumor cell cultures multiplied at about the same rate as the normal human bladder epithelial cells, whereas the other proliferated more slowly. The growth rate of none of the tumor cell cultures had declined at the time of culture termination, but in one of the cultures, small holes developed in the cell sheet as the culture matured in passages 8 and 9. This tumor culture and the slower-growing tumor culture formed sheets of cells, most of the area of which became visibly multilayered as they multiplied to fill the culture vessel, whereas the third culture seemed to form a definite monolayer of cells. Shallow domes formed in cultures of this third strain, and the floating cells that were present at each feeding seemed to come from tops of domes that had sheared off. Some of these floating cells from passage five, when replated onto a collagen-coated surface, reattached and began to proliferate without feeders, although not as rapidly as cells plated with feeders. Cells from the other two tumors did not proliferate when plated alone.

Cells from the dome-forming, monolayer tumor culture expressed the same combination of antigens as normal human bladder epithelial cells, namely, keratins 7, 10, 11, 18, and 19, and, as with the normal human bladder epithelial cells, no keratin 14 or vimentin. Tight junctions also connected these cells (again, see Table 3). There were two significant differences, however, between antigen expression in the normal and tumor cultures. First, normal human bladder epithelial cells expressed keratin 7 throughout the cells but particularly in the cytoplasm, whereas staining of the tumor human bladder epithelial cells was particularly strong in the nucleus, and very much lighter in the cytoplasm (not shown). Secondly, although umbrella cells were visible in all of the fields of normal human bladder epithelial cells stained with antibodies to keratins 18 and 19, none of the fields of tumor cells studied contained cells resembling umbrella cells.

An antibody to uroplakin m stained colonies of both normal and tumor strains. The staining pattern differed from that of the keratins in that little cellular detail was evident. Each colony appeared as one bright blotch instead of a ring comprised of many separate cellular units (not shown). In contrast, this antibody stained the LA7 feeder cells so that cellular details were visible and each cell was distinct from the next.

Figure 7:
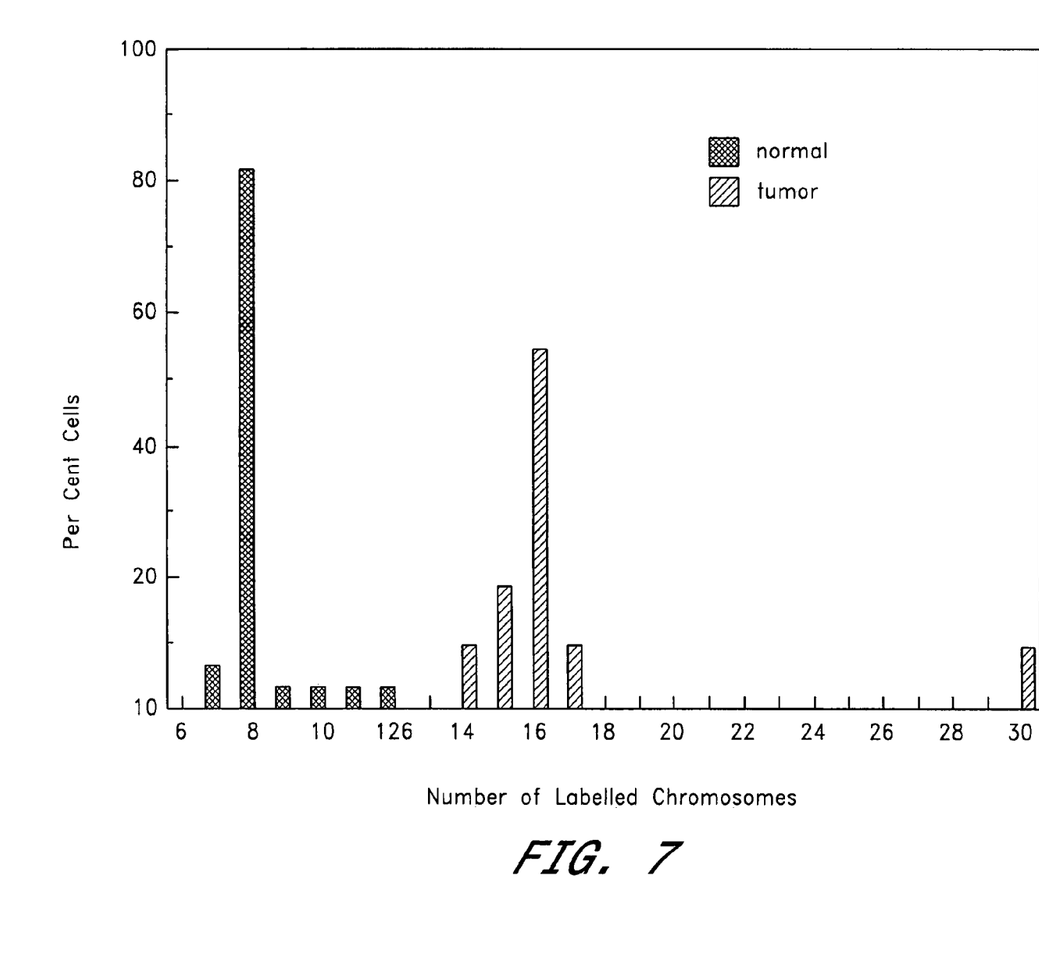
FIG. 7 reports the ploidy of cultured normal and tumor human bladder epithelial cells. Normal cells carry a diploid complement of chromosomes, whereas the tumor cells were mostly tetraploid.

The chromosome complements of one normal strain and the monolayer-forming tumor strain were estimated by counting four differently colored fluorescently labeled chromosomes in each cell. The modal number of fluorescent spots in the normal strain in passage 6 was eight (FIG. 7), indicating that most cells were diploid. In contrast, the modal number of spots for the tumor strain in passage 5 was 16, indicating tetraploidy in this strain.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, composition of matter, process or assay to the objective, spirit and scope of the present invention. All such modifications are intended to be within the scope of the invention.

All references cited herein are to aid in the understanding of the invention, and are incorporated in their entireties for all purposes.

What is claimed is:

1. A method of culturing normal human bladder epithelial cells comprising:
    plating a confluent monolayer of non-proliferating epithelial cells and normal human bladder epithelial cells in medium on a culture support; and
    incubating the plated cells under conditions appropriate to allow the normal human bladder epithelial cells to proliferate;
    wherein the non-proliferating epithelial cells have been mitotically inactivated to be non-proliferating.

2. A normal human bladder epithelial cell culture produced by the method of claim 1.

* * * * *